(12) United States Patent
Rauch

(10) Patent No.: US 8,160,199 B2
(45) Date of Patent: Apr. 17, 2012

(54) SYSTEM FOR 3-DIMENSIONAL MEDICAL IMAGE DATA ACQUISITION

(75) Inventor: John Christopher Rauch, Savoy, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 570 days.

(21) Appl. No.: 12/249,652

(22) Filed: Oct. 10, 2008

(65) Prior Publication Data

US 2009/0097612 A1  Apr. 16, 2009

Related U.S. Application Data

(60) Provisional application No. 60/979,536, filed on Oct. 12, 2007.

(51) Int. Cl.
*A61B 6/03* (2006.01)
(52) U.S. Cl. ............. 378/4; 378/210; 378/901; 382/131
(58) Field of Classification Search .................. 378/210, 378/901, 4–20; 382/128–134
See application file for complete search history.

(56) References Cited

U.S. PATENT DOCUMENTS

| | | | |
|---|---|---|---|
| 4,894,855 A | | 1/1990 | Kresse |
| 5,485,502 A | * | 1/1996 | Hinton et al. ................. 378/117 |
| 6,148,056 A | | 11/2000 | Lin et al. |
| 6,154,515 A | | 11/2000 | Lin et al. |
| 2003/0202637 A1 | * | 10/2003 | Yang ............................ 378/210 |
| 2004/0066908 A1 | * | 4/2004 | Hanke et al. .................. 378/901 |
| 2007/0104309 A1 | * | 5/2007 | Schonborn et al. ............... 378/4 |
| 2008/0240363 A1 | * | 10/2008 | Grebner et al. ............... 378/198 |
| 2008/0310584 A1 | * | 12/2008 | Hey et al. ........................ 378/15 |
| 2009/0262886 A1 | * | 10/2009 | Mollus et al. ................... 378/19 |

FOREIGN PATENT DOCUMENTS

| | | |
|---|---|---|
| DE | 102005004502 A1 * | 8/2006 |
| DE | 102005012700 A1 * | 9/2006 |
| WO | WO 2006116316 A2 * | 11/2006 |

OTHER PUBLICATIONS

Brown et al., Reduction of Aneurysm Clip artifacts on CT Angiograms: A Technical Note, 1999, AJNR Am J Neuroradiol, vol. 20, pp. 694-696.*
Tita et al., Free isocentric 3D imaging and a novel approach for wobble trajectories using a modified standard c-arm, Aug. 2007, Proceedings of the 29th Annual International Conference of the IEEE EMBS, pp. 4418-4421.*
Yang et al., Closed Sinusoid Trajectory for C-Arm CT Imaging, 2006 IEEE Nuclear Science Conference Record, pp. 3480-3484.*
Barrett et al., Artifacts in CT: Recognition and Avoidance, 2004, Radiographics, vol. 24, pp. 1679-1691.*
Ramamurthi et al., Exact 3D Cone-Beam Reconstruction from Projections Obtained Over a Wobble Trajectory on a C-arm, 2004, IEEE, pp. 932-935.*

* cited by examiner

*Primary Examiner* — Edward Glick
*Assistant Examiner* — John Corbett
(74) *Attorney, Agent, or Firm* — Alexander J Burke

(57) ABSTRACT

A method and system provides medical image processing and 3-dimensional image construction of an examination subject. A user is enabled to selectively orient an x-ray imaging system having a variable 3-dimensional acquisition axis relative to an examination subject support for holding an examination subject. A non-planar image data acquisition path is set for the x-ray imaging system oriented around the variable 3-dimensional acquisition axis in response to user instruction. Acquisition of image data of the examination subject is initiated by the x-ray imaging system at a plurality of points along the non-planar image data acquisition path. A 3-dimensional image is constructed from the acquired image data such that any metal artifacts introduced by radio-opaque objects within the examination subject are minimized. The 3-dimensional image is displayed.

27 Claims, 18 Drawing Sheets

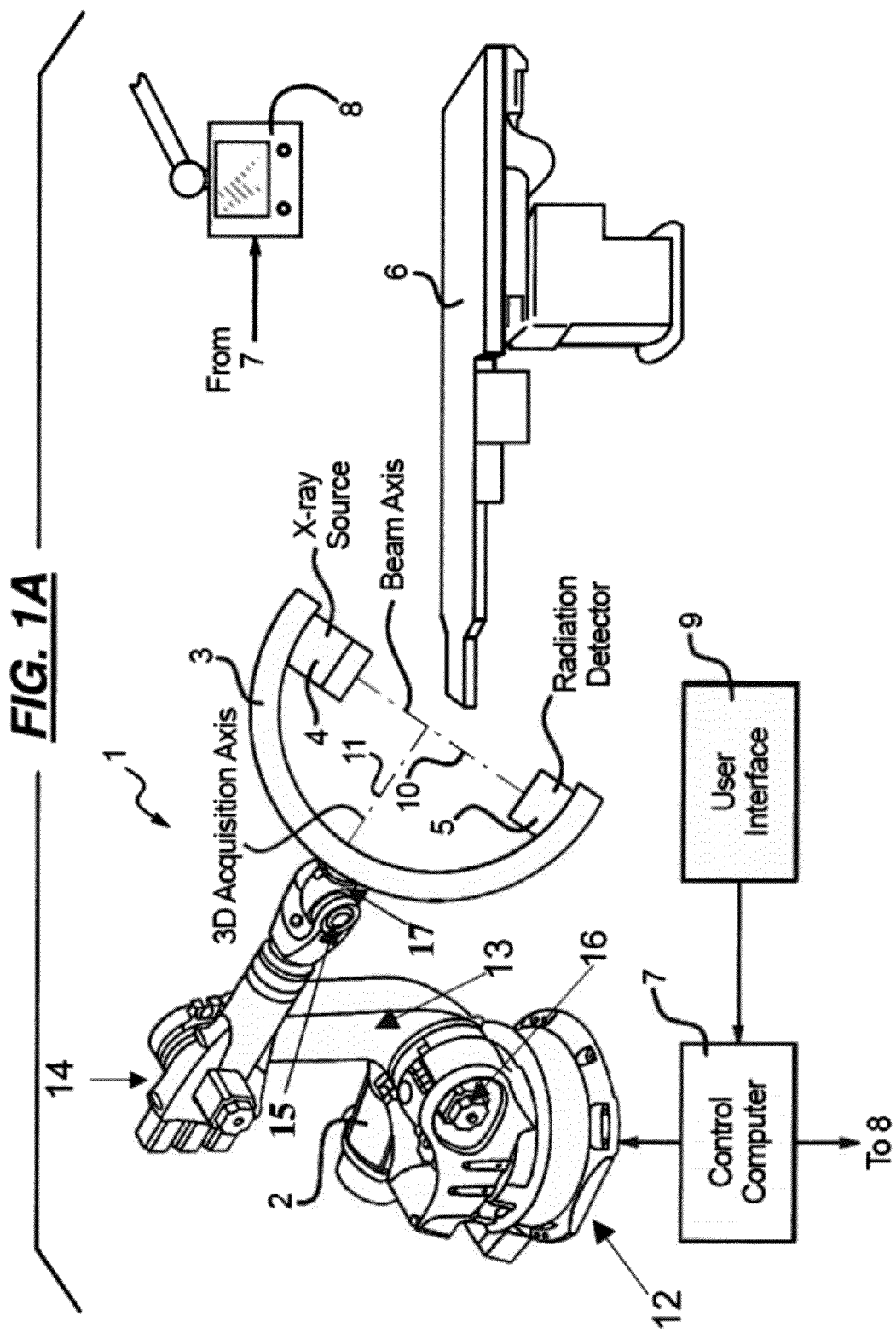

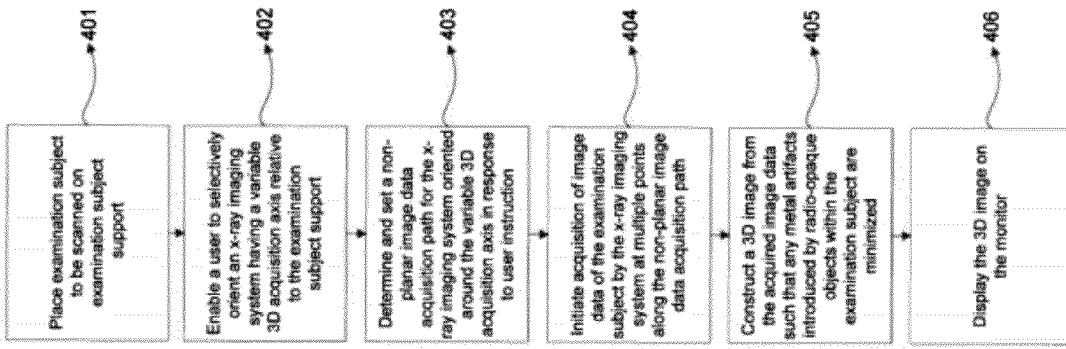

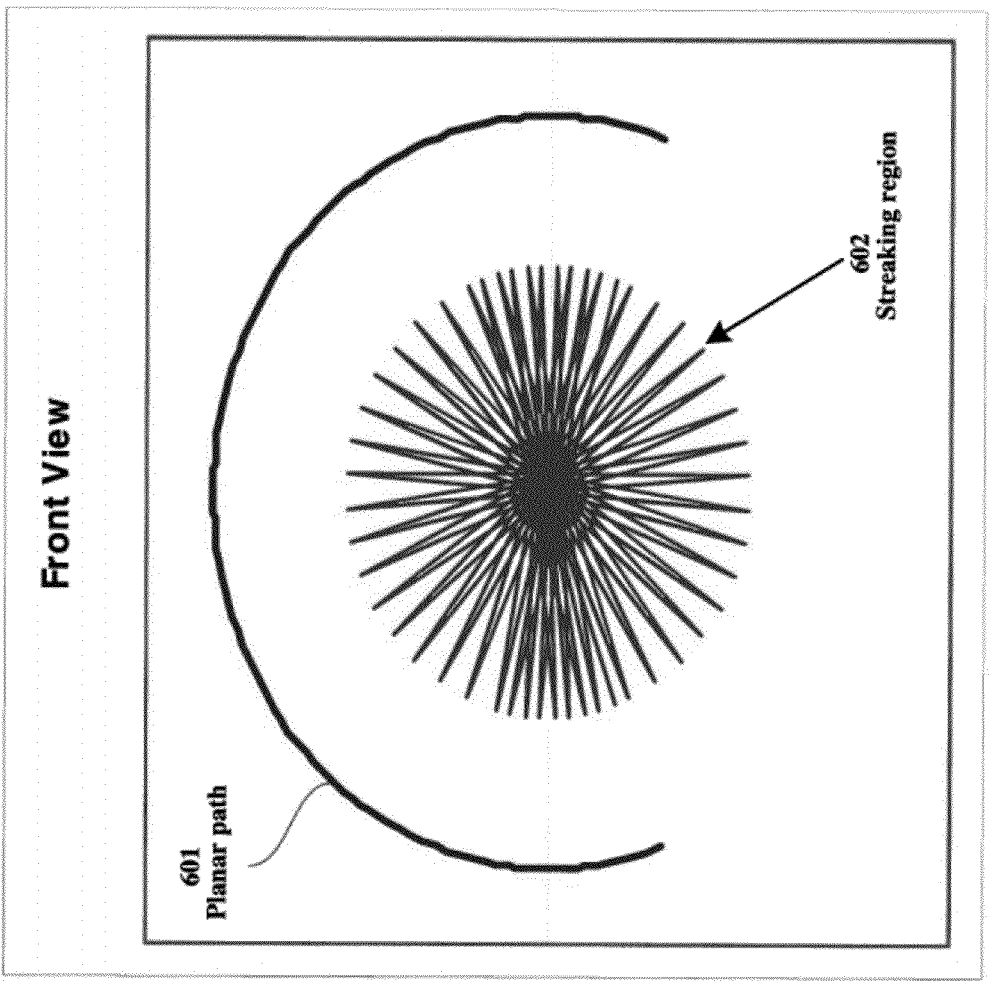

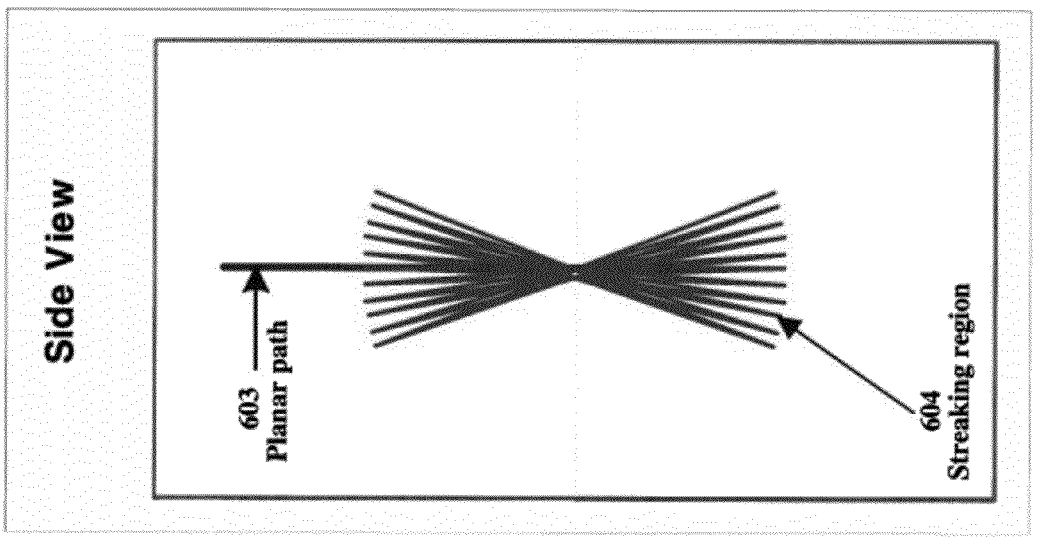

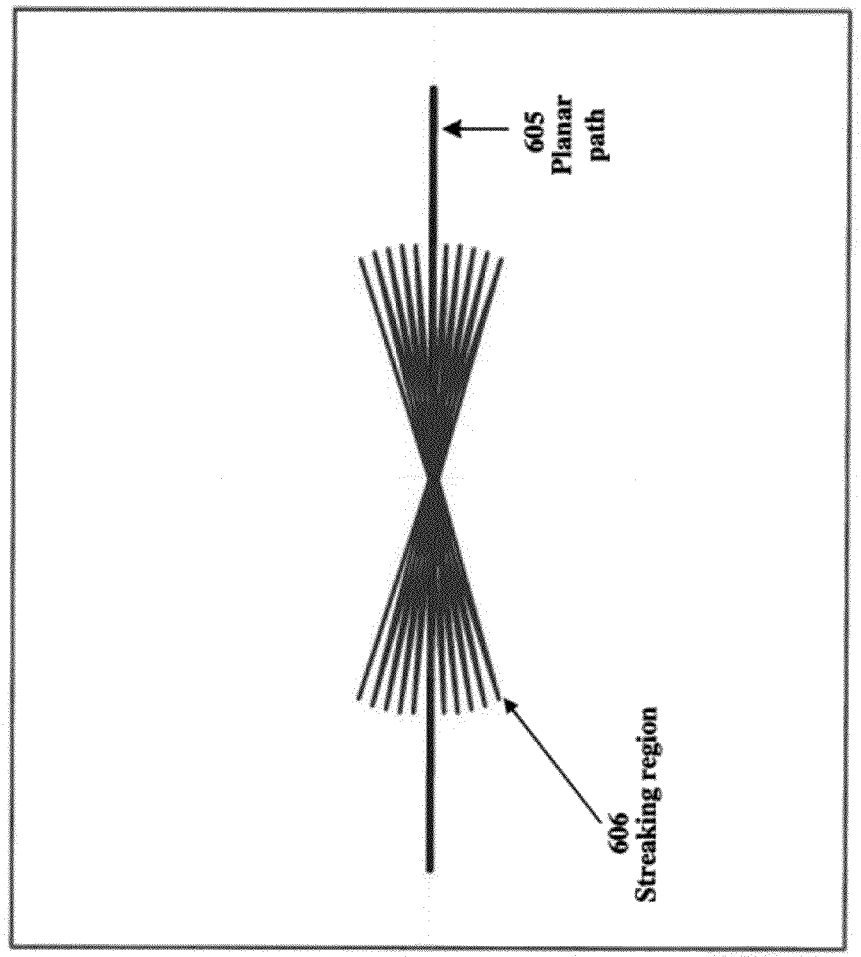
FIG. 6C Top View

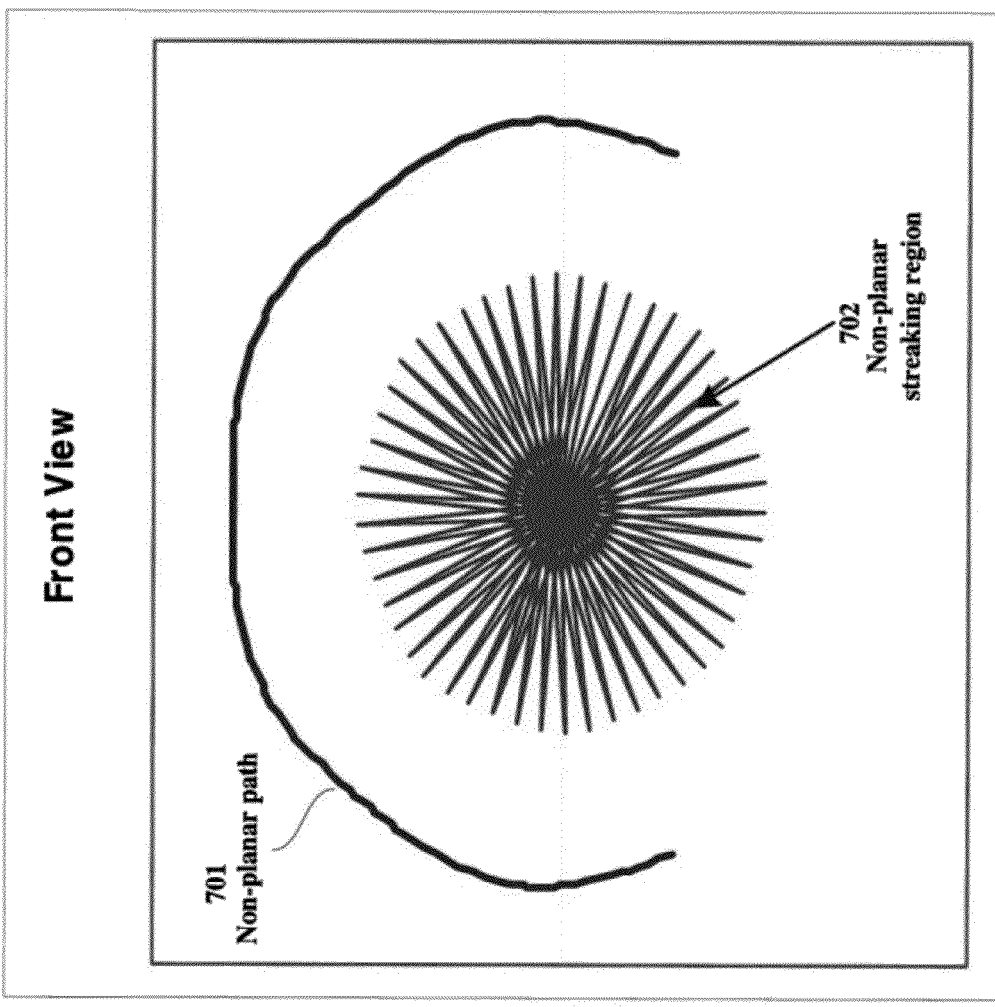

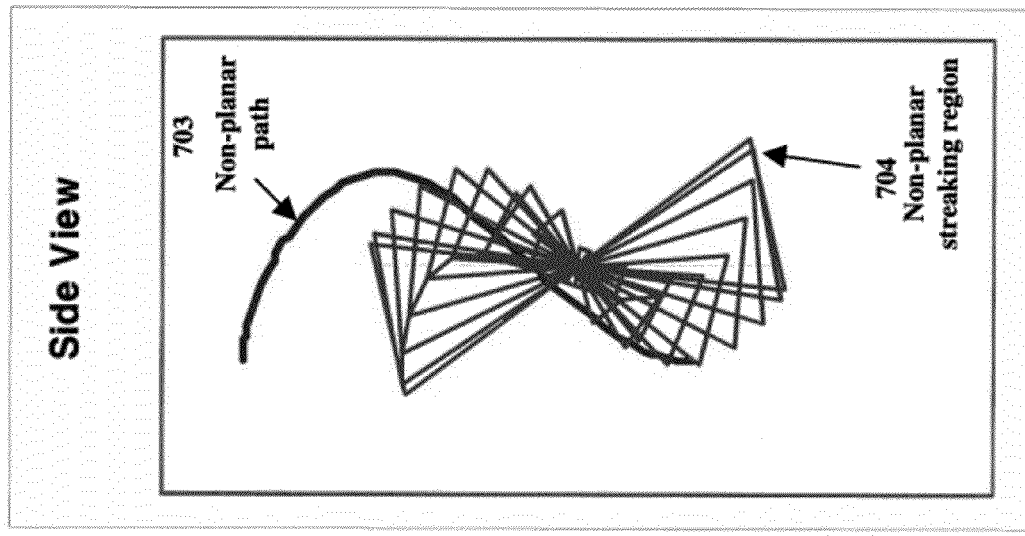

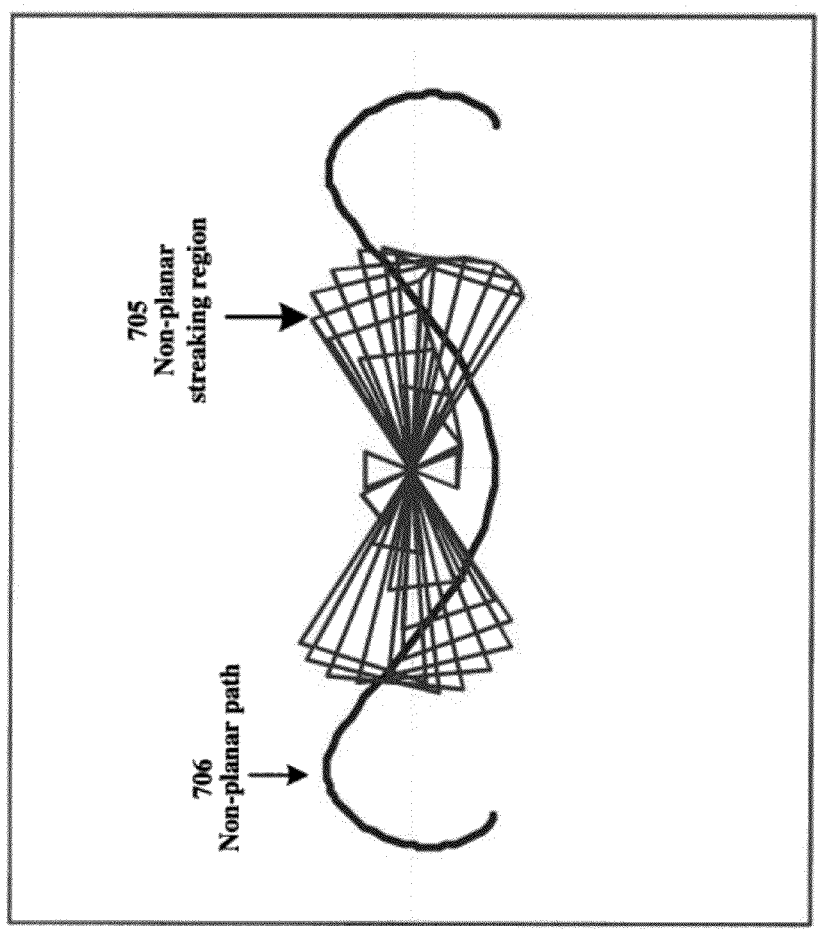

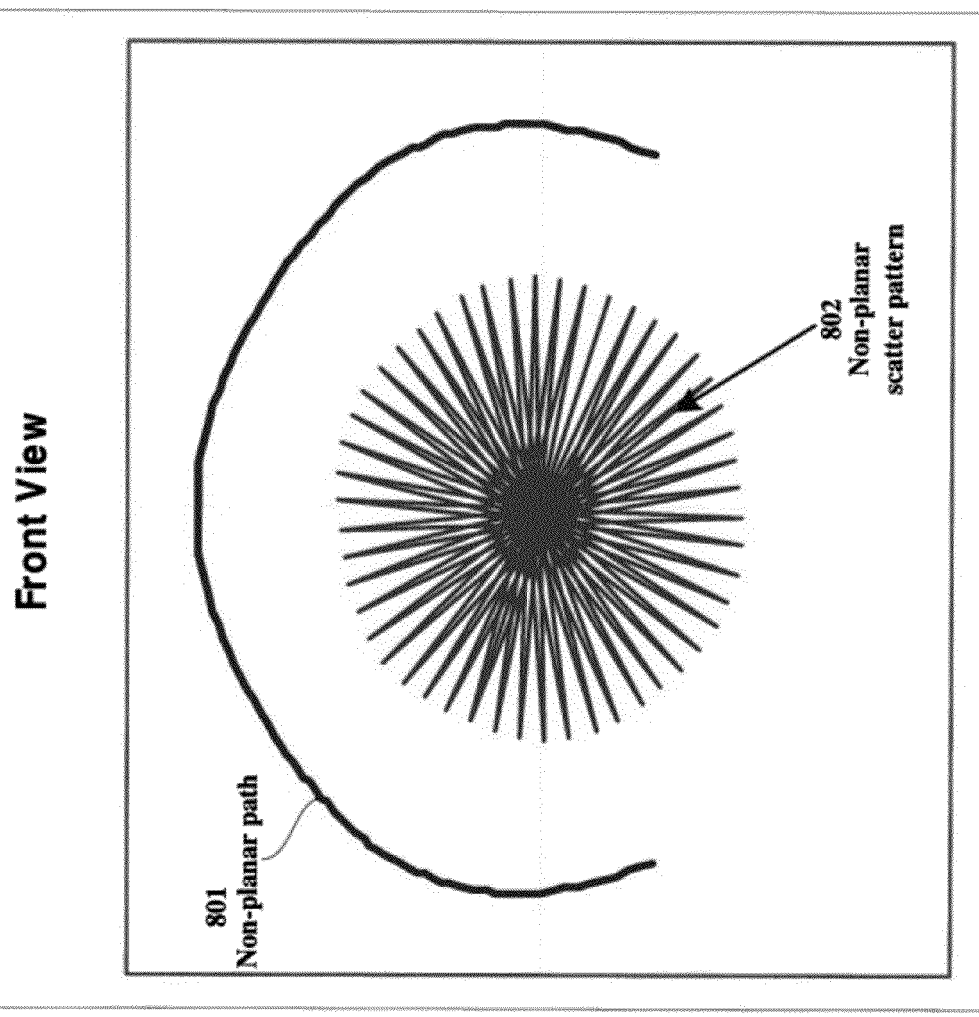

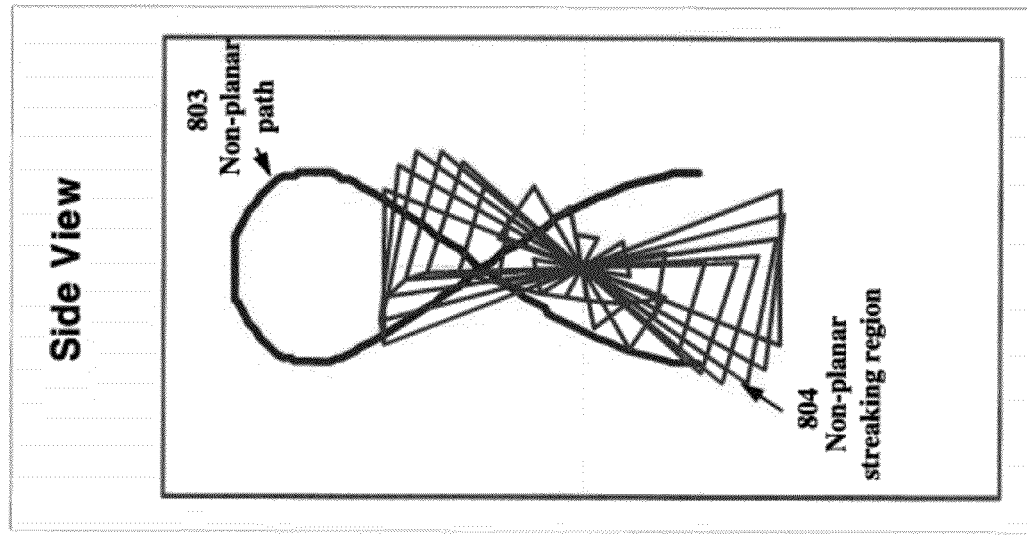

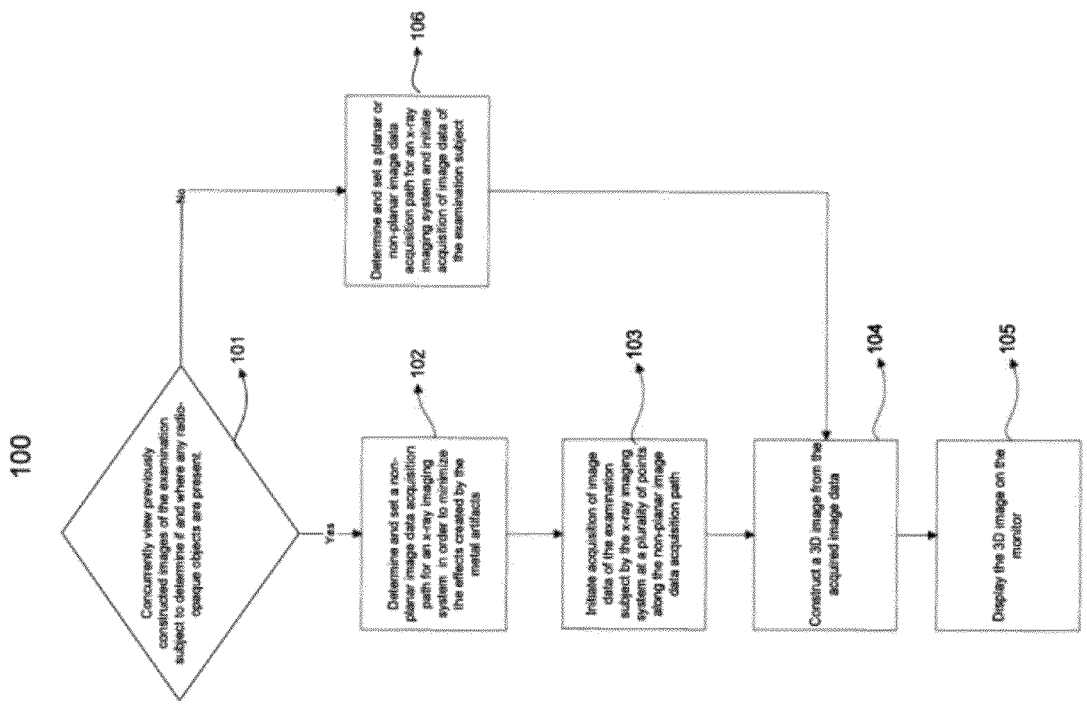

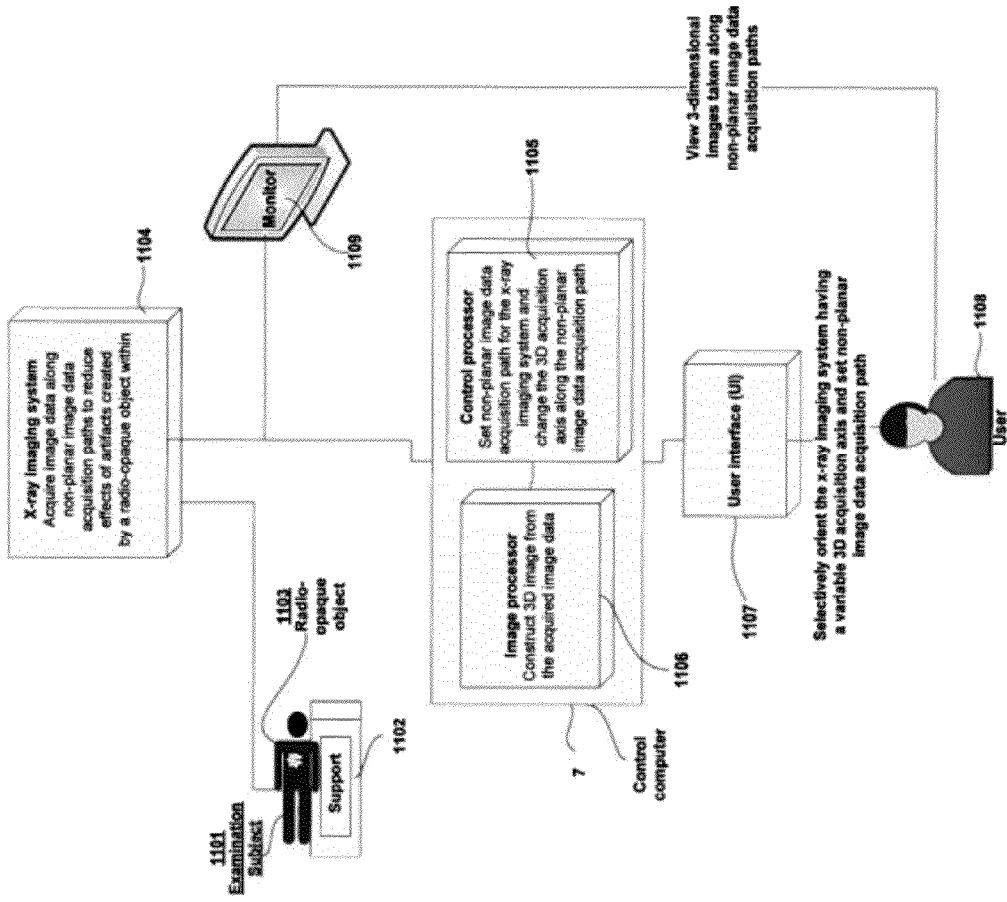

SYSTEM FOR 3-DIMENSIONAL MEDICAL IMAGE DATA ACQUISITION

This is a non-provisional application of U.S. Provisional Application Ser. No. 60/979,536 filed Oct. 12, 2007, by John Rauch.

FIELD OF THE INVENTION

This invention concerns non-planar imaging data acquisition in an x-ray imaging system that improves image quality by diffusing beam hardening and scatter artifacts that arise from the presence of highly dense objects (e.g. metal) adjacent to or within less dense material.

BACKGROUND OF THE INVENTION

Conventional C-arm X-ray imaging systems acquire images along planar paths having a 3-dimensional acquisition axis. The 3-dimensional acquisition axis is the axis about which the x-ray source and radiation detector, held in fixed geometry by the C-arm, rotate. An examination subject being x-rayed by a conventional imaging system may have highly dense, radio-opaque objects (e.g. dental fillings, aneurysm clips or stents, screws, plates, etc.) disposed at various points through his/her body. These radio-opaque objects may include metals or other dense materials. When attempting to capture an image of an area of an examination subject's anatomy proximate the radio-opaque object(s), high x-ray absorption and deflection or scatter of the x-rays is directed at these objects. The deflected and scattered x-rays are picked up by the radiation detector at various locations other than their anticipated path from the source to the radiation detector. When the x-rays are deflected and strike the radiation detector, added noise is introduced into the x-ray image data. While some absorption and scatter is expected, the increased or complete absorption due to the presence of highly dense objects in the subject being imaged will result in artifact(s) obscuring the surrounding anatomy that is of interest. These artifact(s) include at least one of beam hardening artifacts and scatter artifacts. Beam hardening artifacts arise when x-rays are completely blocked from reaching the radiation detector due to the presence of highly dense objects. The presence of beam hardening artifacts produces streaking in the x-ray images. Scatter artifact occurs when dense objects deflect the x-rays and redirect them in different directions. When the x-rays strike the radiation detector, artifacts will result which effect image quality of the x-ray images. These artifact(s) created by the presence of metal or similarly dense radio opaque objects within the examination subject being x-rayed are hereinafter referred to as "metal artifacts." These metal artifacts degrade the quality of the 3-dimensional image to be constructed. These metal artifacts are manifested in the 3-dimensional image as lines emanating from and extending radially away from the object. The metal artifacts raise the intensity value of voxels (a combination of the words volumetric and pixels) along these lines with a maximum increase in intensity proximal to the object and decreasing intensity moving away from the object. The term voxel refers to a volume element in 3-dimensional space. A voxel in 3-dimensional space is analogous to a pixel in 2-dimensional space. The metal artifacts are worst along the path of the x-ray beams as they pass through the radio-opaque object(s). By nature of conventional scanning geometry (rotation of the source and detector within a single plane) the metal artifacts are most prominent and create the most effects adjacent to the radio-opaque object and in the plane of rotation—within the acquisition plane. This means that metal artifacts in the 3-dimensional (CT) image are fixed and are largely constrained to the planes containing the radio-opaque object generating the metal artifacts and perpendicular to the 3-dimensional acquisition axis. The 3-dimensional acquisition axis is the axis about which the x-ray source and radiation detector rotate.

If the region of interest in the examination subject happens to lie adjacent to the radio-opaque object and in a direction perpendicular to the 3-dimensional acquisition axis, the metal artifacts in the image significantly degrade and even preclude an accurate diagnosis of the region of interest when the images are acquired along a planar path. A path, as used hereinafter, refers to the route along which the image acquisition system travels. A planar path refers to a path along a single plane.

FIGS. 2 and 3 illustrate the planar 3-dimensional acquisition problem caused by metal artifacts introduced by a radio-opaque object inside the examination subject along a single plane. The planar 3-dimensional path is defined by the rotation of the x-ray source and radiation detector about a single, fixed rotation axis 204. Metal artifacts 201 are formed by a previously-implanted platinum coil, which has been implanted in the examination subject being imaged in order to treat an aneurysm. The platinum coil mass 202 is located in close proximity to a vessel, which contains a stenosis 205. It is desirable to obtain a 3-dimensional constructed image of the examination subject that accurately depicts the vessel containing the stenosis 205 along with its location with respect to the coil mass 202 and other anatomy. This image is used to quantify the stenosis 205 and evaluate treatment options (e.g. angioplasty, stenting or stenting with angioplasty). However, metal artifacts 201 produced in a constructed 3-dimensional image taken along a planar path obscures the stenosis 205. The effects of the metal artifacts are worst and degrade the image most in the path of the x-ray beam and adjacent to the radio-opaque object(s) causing the metal artifacts.

FIG. 3 further shows the effects of metal artifacts 301 each time the x-ray imaging system is rotated and image data is acquired. FIGS. 2 and 3 show a situation where the axis of rotation is perpendicular to the image (e.g. coming out of the image toward the reader). In this arrangement, the metal artifacts branch out from a fan beam 203 in FIGS. 2 and 3. In the planar acquisition situation, as depicted in FIGS. 2 and 3, the number of projections that contain metal artifacts for areas around the radio-opaque object greatly outnumbers the number of projections that do not contain metal artifacts. When the ratio of the number of projections that contain metal artifacts to those that do not is high, more metal artifacts are present in the constructed image.

Metal artifact is sometimes moved away from a region of interest by changing the anatomical geometry of the examination subject with respect to the acquisition axis. For example, if an examination subject has dental fillings the examination subject is moved with relation to the scanner by tilting the head to shift metal artifacts created from dental fillings away from a particular region of interest (e.g. skull base or carotid arteries). However, moving the examination subject may not always be viable as it is not always possible to reorient the examination subject's anatomy with respect to the table support. Tilting the examination subject's head is hindered by the presence of a breathing tube or is precluded by a need to maintain examination subject's current positioning.

In computed tomography (CT) scanners the rotation plane is titled with respect to the examination subject (by applying a gantry tilt in a cranial or caudal direction), allowing the metal artifacts to be shifted without moving the examination subject. A "cranial" direction of movement is movement from the patient's middle toward the patient's head, while a "caudal" direction of movement is a movement from the patient's middle toward the patient's feet. Known C-arm X-ray imaging systems acquire 3-dimensional images by rotating the source and detector (fixed in geometric relationship by the C-arm) of the imaging system about a system specified acquisition axis. This rotation about a single acquisition axis forces a beam axis to be contained in a single plane, throughout the movement of the C-arm. This acquisition geometry places the majority of metal artifact adjacent to the artifact generating object and within planes in the reconstructed image that are parallel to the acquisition plane (perpendicular the acquisition axis). As seen in FIGS. 2 and 3, metal artifact can negatively affect the readability and diagnostic value of the acquired images and, by virtue of the mechanism by which the imaging data is acquired, the metal artifact is focused in the acquisition plane.

Additionally, a great deal of effort has been spent improving the quality of 3-dimensional images that contain metal artifacts, by attempting to improve the quality of the data within the signals acquired. However, solutions that shift metal artifacts within the image do not reduce the overall effect of the metal artifacts in the image because the image data is acquired along a planar path. Image data acquired along a planar path will still contain the effects of metal artifacts. Several post processing techniques to reduce the overall effect of metal artifacts have been made. The main disadvantage of post processing techniques to reduce overall effects of the metal artifacts is that the metal artifacts exist in the image data acquired. There is a need to reduce the overall effects of the metal artifacts present in the image data acquired. A system according to invention principles addresses these deficiencies and related problems.

SUMMARY OF THE INVENTION

The inventor has advantageously recognized it is desirable to have a system that minimizes the effects of metal artifacts and acquires image data along a non-planar image data acquisition path to minimize or reduce the effects of metal artifacts introduced by radio-opaque objects within an examination subject being examined. Further, the same image quality enhancement post processing techniques used on planar 3-dimensional acquisitions are usable on the images acquired from non-planar image data acquisitions. A method provides medical image processing and 3-dimensional image construction of an examination subject. A user is enabled to selectively orient an x-ray imaging system having a variable 3-dimensional acquisition axis relative to an examination subject support for holding an examination subject. A non-planar image data acquisition path is set for the x-ray imaging system oriented around the variable 3-dimensional acquisition axis in response to user instruction. Acquisition of image data of the examination subject is initiated by the x-ray imaging system at a plurality of points along the non-planar image data acquisition path. A 3-dimensional image is constructed from the acquired image data such that any metal artifacts introduced by radio-opaque objects within the examination subject are minimized. The 3-dimensional image is displayed.

A system provides medical image processing and 3-dimensional image construction of an examination subject. An examination subject is placed on a support surface such as a bed. An x-ray imaging system acquires image data. The x-ray imaging system has a variable 3-dimensional acquisition axis relative to the examination subject on the support surface. A control processor, electrically coupled to the x-ray imaging system, enables a user to set a non-planar image data acquisition path for the x-ray imaging system oriented around the variable 3-dimensional acquisition axis. In response to user instruction, image data of the examination subject is acquired by the x-ray imaging system at a plurality of points along the non-planar image data acquisition path. An image processor constructs a 3-dimensional image from the acquired image data and minimizes metal artifacts introduced by any radio-opaque objects within the examination subject. A monitor displays the 3-dimensional image.

BRIEF DESCRIPTION OF THE DRAWING

FIG. 1A illustrates components of an x-ray imaging system suitable for use in accordance with the invention principles.

FIG. 4 illustrates a flowchart detailing the operation of the system in accordance with the invention principles.

FIG. 6A illustrates a front view of a planar scan path and streaking created by effects of metal artifacts.

FIG. 6B illustrates a side view of a planar scan path and streaking created by effects of metal artifacts.

FIG. 6C illustrates a top view of a planar scan path and streaking created by effects of metal artifacts.

FIG. 7A illustrates a front view of a non-planar scan path and streaking created by effects of metal artifacts.

FIG. 7B illustrates a side view of a non-planar scan path and streaking created by effects of metal artifacts.

FIG. 7C illustrates a top view of a non-planar scan path and streaking created by effects of metal artifacts.

FIG. 8A illustrates a front view of an additional non-planar scan path and streaking created by effects of metal artifacts.

FIG. 8B illustrates a side view of an additional non-planar scan path and streaking created by effects of metal artifacts.

FIG. 10 illustrates a flowchart showing the events that occur after viewing a previously constructed 3-dimensional image of the examination subject to determine if and where any radio-opaque objects are present within.

FIG. 11 illustrates a block diagram of an examination subject being examined by the x-ray imaging system in accordance with the principles of the invention.

DETAILED DESCRIPTION OF THE INVENTION

Figure 1B:
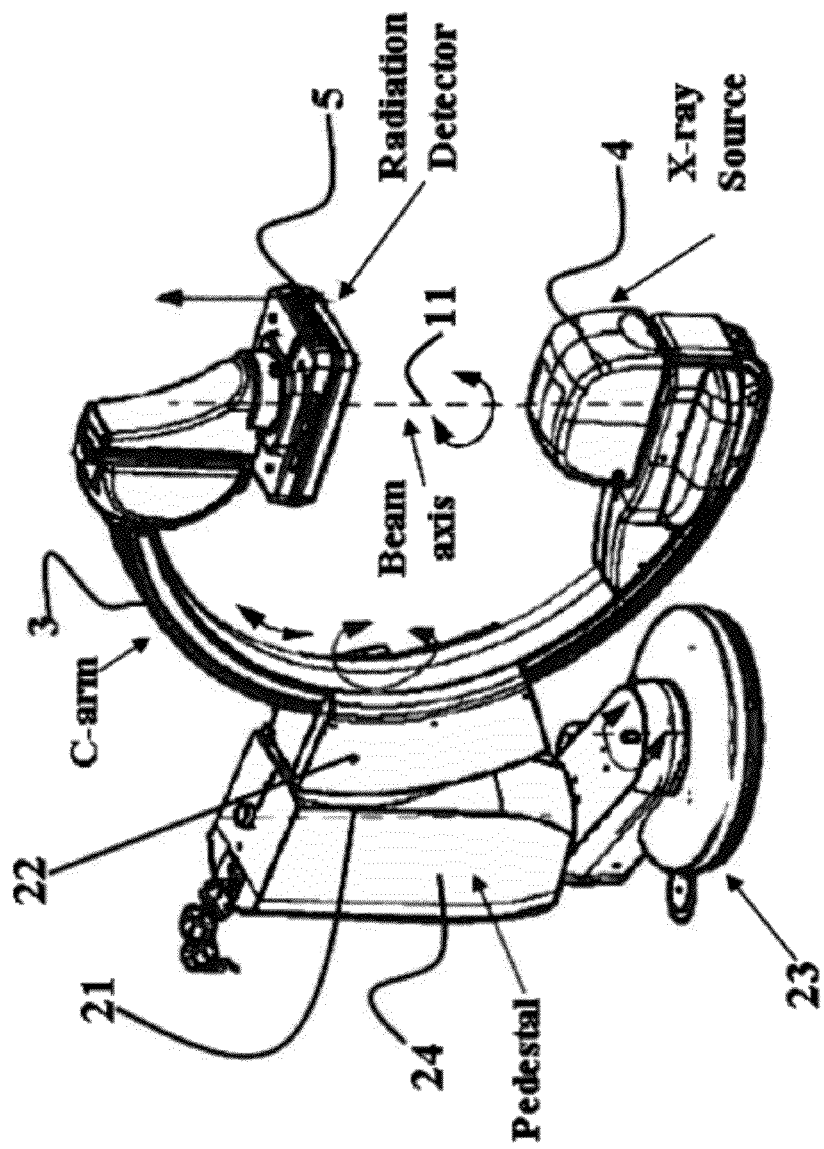
FIG. 1B illustrates components of a rotational C-arm and pedestal system suitable for use in accordance with the invention principles.
Figure 2:
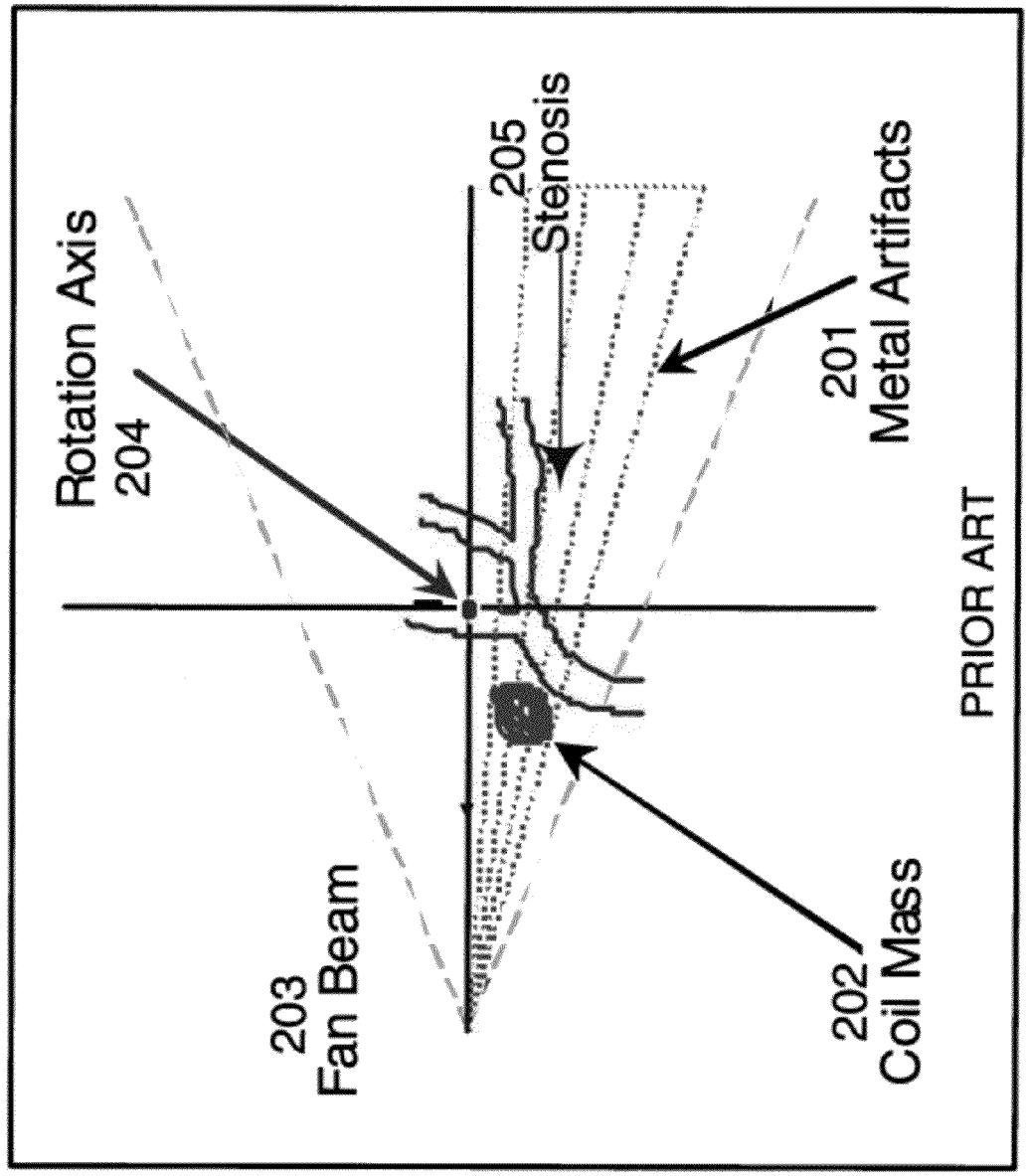
FIG. 2 schematically illustrates a planar 3-dimensional acquisition problem experienced by prior art caused by metal artifacts introduced and contained within a single plane.
Figure 3:
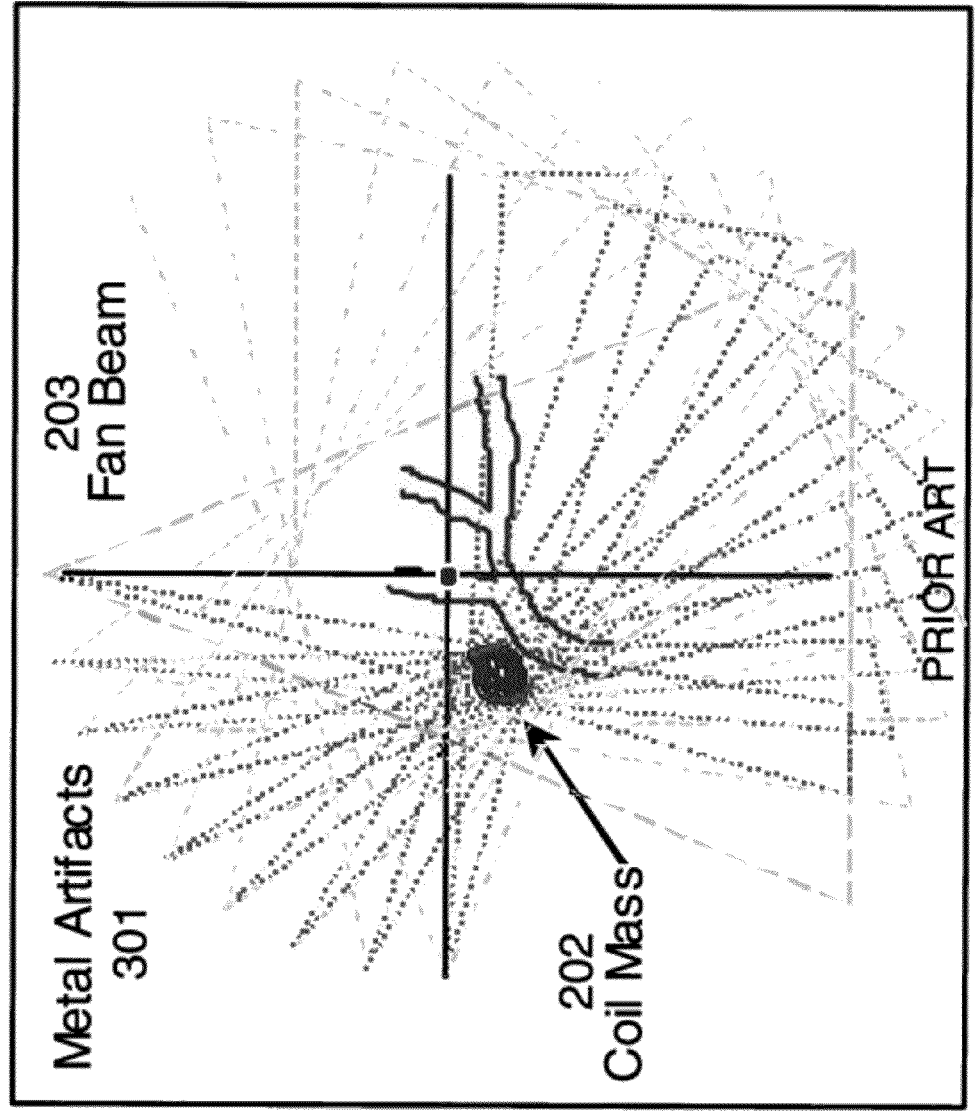
FIG. 3 schematically illustrates a planar 3-dimensional acquisition problem experienced by prior art caused by containing metal artifacts introduced and contained within a single plane of an x-ray imaging system that is rotated.

Known x-ray imaging systems for acquiring images of an examination subject containing a radio-opaque object produce poor quality images because of the metal artifacts introduced in the image. Radio-opaque objects are objects that do not allow x-rays or other types of radiation penetrate. Since radio-opaque objects block radiation, it is difficult to x-ray an examination subject that contains a radio-opaque object inside his/her body. Additionally, these radio-opaque objects create metal artifacts caused by beam hardening or scatter artifacts that can degrade the quality of an x-ray image. Known systems shift the examination subject and/or the examination subject support to shift the primary effect of metal artifacts away from an area of interest to other areas in the image, improving image quality for a specific area. However, in these systems, the image data is acquired along planar paths. Therefore, the metal artifacts introduced in the 3-dimensional image by radio-opaque objects within the examination subject are focused into the planes parallel to the planar path. A system according to invention principles acquires image data along at a plurality of points along a non-planar image data acquisition path to diffuse the metal artifact in the direction of additional planes producing the net effect of reducing metal artifacts introduced by radio-opaque objects within an examination subject being examined. Metal artifacts are still present, but it is diffused over a larger volume in which additional projections are available to reduce the overall effect. Although the invention describes reducing metal artifacts created by beam hardening, the same principles can be applied to the reduction of scatter artifacts. Additionally, a non-planar path is different from a planar path which travels along a single plane. A non-planar path does not follow a single plane but is able to travel along and move amongst multiple planes. A non-planar path is a movement of the x-ray source and radiation detector (in fixed geometric relation) wherein the beam axis (line between the center of the x-ray source and the center of the radiation detector) is not constrained to a single plane.

FIG. 1A illustrates the basic components of an x-ray imaging system. The system includes a robotic C-arm system 1, which has a multi-axis robot 2 to which a C-arm 3 is movably mounted. The C-arm 3 is movable in a manner providing a 360 degree range of motion (i.e., orbital movement and rotation movement) in any direction. The robot 2 provides the C-arm 3 with 360 degrees range of motion. The rotation and orbital movements of the C-arm 3 itself are effected at the wrist joint 15 of the robot 2 and the two-part arm 13 of the robot 2 is articulated at an elbow joint 14 and is also articulated at a shoulder joint 16, where the arm 13 is attached to the base 12. The base 12 is rotatable around a vertical axis proceeding perpendicular to the floor on which the base rests.

The C-arm 3 carries an x-ray source 4 and a radiation detector 5 at the opposite free ends thereof. The overall orientation of the C-arm 3, having a radiation detector 5 and an x-ray source 4 facing each other on opposing ends of the C-arm 3, is connected to and selectively adjusted in space by the multi-axis robot 2. Therefore, the C-arm 3 can move with 360 degrees range of motion. The elbow joint 14, wrist joint 15 and shoulder joint 16 of the robotic C-arm system 1 allow the x-ray source 4 and the radiation detector 5, facing each other on opposing ends of the C-arm 3, to move 360 degrees and assume any position with respect to an examination subject support 6 on which an examination subject lies. Additionally, the multi-axis robot 2 can rotate the C-arm 3 independent of any other motion about a 3-dimensional axis 11 via a pivot mechanism 17 located inside the wrist joint 17. The x-ray source 4 emits radiation directed at an examination subject and projects radiation onto the radiation detector 5 along a beam axis 10. The radiation detector 5 is a flat panel radiation detector that is used to detect radiation attenuated by the examination subject in a CT mode or a fluoroscopy mode. The C-arm system 1 has a variable 3-dimensional acquisition axis 11. The flexibility in movement afforded by the C-arm system 1 provides the ability to acquire 3-dimensional image data while varying the position of the 3D acquisition axis 11. Movements as well as the image acquisition are controlled by a control computer 7. The resulting image or images are displayed at monitor 8 that is in communication with the control computer 7. The robotic C-arm system 1 is used to obtain a plurality of individual images that are used to construct 3-dimensional image of the area of interest of the examination subject on the examination subject support 6. It should also be appreciated that the examination subject need not be positioned on support 6 and is positioned and supported in any manner that allows the C-arm 3 to be moved about the body of the examination subject. A user makes suitable entries into the control computer 7 via a user interface 9 to select the position of the C-arm 3 in an orientation that positions the C-arm 3 to acquire image data at a plurality of points along a non-planar image data acquisition path.

FIG. 1B illustrates an alternate C-arm system 20. The C-arm 3 is connected to a support 24 via a bracket 22. The bracket 22 allows the C-arm to slide in an orbital movement in a cranial-caudal direction indicated by the orbital arrows. The C-arm 3 may also rotate about a connection point 21 (partially hidden view shown in FIG. 1B). The support 24 is held in place by a base 23. The C-arm 3 includes a radiation detector 5 and an x-ray source 4 facing each other on opposing ends and are in a fixed geometry with respect to the acquisition axis. The C-arm 3 is connected to and selectively adjusted in space by the support 24. A non-planar image data acquisition path can be obtained by the movement of the C-arm system 20 by coordinating the sliding motion of bracket 22 with the rotational motion enabled by connection point 21. Specifically, in the case of a non-planar image data acquisition path, the beam axis 11 is not constrained to a single plane and may move into and out of multiple planes. The exemplary angiography system of FIG. 1B shows the support 24 as a pedestal. However, it should be appreciated that a plurality of different types of supports 24 for angiography system are known and include for example, floor pedestals and ceiling mounted supports and the system according to invention principles may be implemented with any type of support 24.

The present system overcomes the problems of x-ray imaging systems that acquire images at points along planar paths by advantageously acquiring images at a plurality of points along non-planar image data acquisition paths. Acquiring images via a non-planar image data acquisition path advantageously diffuses metal artifacts in multiple planes reducing the effects of the metal artifacts that would normally be contained within a single plane. The system acquires views of regions adjacent to metal artifacts that do not contain the metal artifacts in that view. By acquiring these additional views of the area about the radio-opaque object, the effects of the metal artifacts in the region of interest are reduced.

The process of constructing a 3-dimensional image utilizes multiple projections (views) of the examination subject taken at multiple different orientations. The more projections acquired, the better the quality of the image. With a sufficient number of projections acquired at orientations that circumscribe the examination subject a high quality 3-dimensional image is constructed using image processing algorithms implemented in electronic circuitry or software or any combination thereof. Additionally, image quality is improved by diffusing beam hardening artifacts that arise by the presence of highly dense objects (e.g. metal) adjacent to or within less dense material (e.g. tissue). The non-planar image data acquisition path provides direct views of the material adjacent to a metal artifact generating object that does not contain the object. This improved acquired image projection is used in conjunction with other acquired image projections and therefore improves the quality of the constructed 3-dimensional image.

FIG. 4 is a flowchart 400 detailing the operation of the non-planar image acquisition system. As seen in step 401, an examination subject that is to be x-rayed or scanned is placed on an examination subject support. Alternatively, the examination subject is positioned such that the x-ray imaging system moves about the subject. In step 402, a user selectively orients an x-ray imaging system with a variable 3-dimensional acquisition axis relative to the examination subject support. As seen in step 403, a non-planar image data acquisition path for the x-ray imaging system is determined and set in response to user instruction. In step 404, acquisition of the image data of the examination subject is initiated by the x-ray imaging system at multiple points along the non-planar image data acquisition path. In step 405, a 3-dimensional image is constructed from the acquired image data at the points along the non-planar image acquisition path. As the image data is acquired over the non-planar image acquisition path, the effects of any metal artifacts introduced by radio-opaque objects within the examination subject are minimized in each acquired image projection which is used in constructing a 3 dimensional image of the examination subject. The non-planar image acquisition path captures image data at a plurality of points along multiple planes and therefore, the metal artifacts are diffused into other planes which more evenly distribute the effects of the metal artifacts. Capturing image data at a plurality of points along the non-planar image acquisition path is better than capturing image data at points along a single planar path, as it acquires projection data that reduces the effects of metal artifact in the reconstructed 3-dimension image. The 3-dimensional acquisition axis is adjusted by automatically changing the non-planar image data acquisition path in order to minimize the introduced metal artifacts. The 3-dimensional image, in which the overall effects of metal artifacts are reduced, is displayed on a monitor, as seen in 406. Alternatively, the 3-dimensional image is output to a printer.

In a further embodiment, the system enables a user to move the examination subject support 6 in a cranial-caudal direction which allows the x-ray imaging system 1 to acquire image data at a plurality of points along the non-planar image data acquisition path. Alternatively, the x-ray imaging system 1 may automatically move in a cranial-caudal direction which allows the x-ray imaging system 1 to acquire image data at a plurality of points along the non-planar image data acquisition path. In addition, a user can move the examination subject support 6 and automatically move the x-ray imaging system 1 in coordination with each other in a cranial-caudal direction which allows the x-ray imaging system 1 to acquire image data at multiple points along the non-planar image data acquisition path, 404. In implementing this embodiment whereby the patient support is moved in conjunction with the x-ray system requires additional parameters be input by a user to enable construction of the 3 dimensional image from the multiple image projections acquired along the non-planar image data acquisition path.

Acquiring image data projection via a non-planar image data acquisition path is advantageous over convention planar image data acquisition. Images acquired at points along a planar path are unable to avoid or minimize the effects of metal artifacts introduced by radio-opaque objects within an examination subject because the images are taken at points along a single plane. One of the difficulties encountered in images taken at points along a single plane containing effects of metal artifacts is that the number of projections containing metal artifacts greatly outnumbers the number of projections without metal artifacts for the areas adjacent to the radio-opaque object. This problem is lessened if a non-planar image data acquisition path is employed.

Figure 5C:
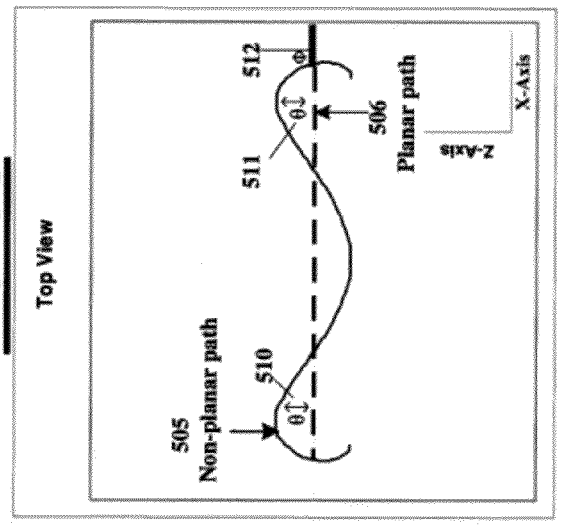
FIG. 5C illustrates a top view of a non-planar scan path compared with a planar scan path.
Figure 5B:
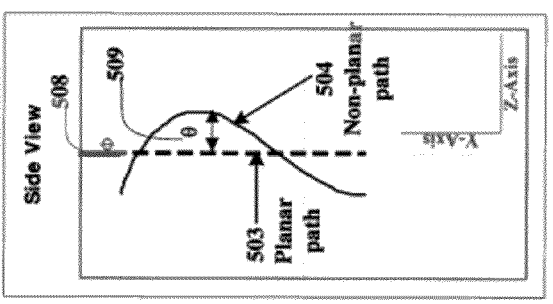
FIG. 5B illustrates a side view of a non-planar scan path compared with a planar scan path.
Figure 5A:
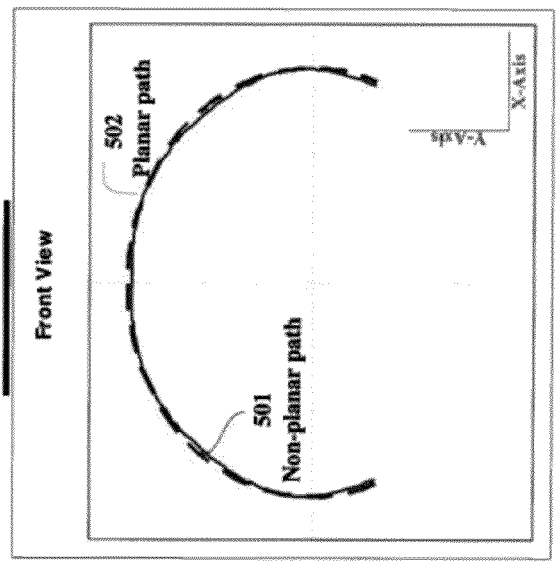
FIG. 5A illustrates a front view of a non-planar scan path compared with a planar scan path.

An exemplary non-planar image data acquisition path according to invention principles is shown contrasted with a conventional planar acquisition in FIGS. 5A, 5B and 5C. The paths shown in FIGS. 5A, 5B and 5C are traversed by the detector 5 of the x-ray imaging system. FIGS. 5A, 5B and 5C are orthogonal views of the image acquisition paths. In each of these figures, the axis indicating the direction of the paths is shown in terms of the x, y and z-axis on the bottom right of the corresponding figure. In FIGS 5A-5C, the non-planar acquisition paths are shown as solid lines and the planar acquisition paths are shown as a dotted line. In FIG. 5A, a front view of the two paths is shown. Non-planar image data acquisition path 501 and planar path 502 are identical in this view and overlap each other. The difference between the non-planar and planar acquisition paths is demonstrated in FIGS. 5B and 5C. FIG. 5B shows the side view of the paths. The planar path 503 in FIG. 5B is a bold, dashed, straight, vertical line along the y-axis on the graph. The non-planar image data acquisition path 504 is a solid, curved substantially s-shaped path that is able to minimize the effects of metal artifacts along the vertical plane. The non-planar path 504 enables acquisition of image data in the area immediately surrounding the radio-opaque object(s) and thus minimizes any metal artifacts created thereby. In contrast, the planar acquisition path acquires image data within the single plane and the acquired image includes the full spectrum of metal artifacts created by the radio-opaque object. FIG. 5C is a top view of the planar and non-planar data acquisition paths. The planar acquisition path 506 is represented by a bold, dashed, straight line extending along the x-axis. The non-planar image data acquisition path 505, represented by a solid line, is able to capture image data at a plurality of points along multiple planes. As seen in FIGS. 5B and 5C, the non-planar image data acquisition path taken by the x-ray detector of the x-ray imaging system is able to capture images at a plurality of points along multiple planes and minimize the effects of artifacts by moving in an acquisition path that includes a plane that is different from the plane in which the radio-opaque object resides. For example, if radio-opaque object(s) are along the planar paths 503 and 506, images acquired at points along those paths will contain the effects of metal artifacts. However, images acquired at a plurality of points along the non-planar image data acquisition paths 504 and 505 acquire some images which minimize or do not contain the effects of metal artifacts. Therefore, the image data acquired at a plurality of points along the non-planar image data acquisition paths are higher quality and contain less metal artifacts than the image data acquired at points along planar paths.

In order to acquire image data at a plurality of points along non-planar image data acquisition paths, the x-ray source 4 and radiation detector 5 are rotated about a rotation axis, but deflect the rotation axis, with respect to the examination subject, as the x-ray source 4 and radiation detector 5 rotate. The rotation of the x-ray source 4 and radiation detector 5 are represented as theta ($\theta$) and the deflection of the rotation axis as phi ($\Phi$), as depicted in FIGS. 5B and 5C. For a conventional scan phi can vary between zero (0) degrees and 180 degrees (plus the half angle of the projection), and theta can be held constant at 0 degrees. For a non-planar scan phi can increase from zero degrees to 180 degrees (plus the half angle of the projection) with theta varying as a function between +10 degrees and −10 degrees (e.g. as a sinusoid or saw tooth waveform). As seen in FIG. 5B, phi 508 is on the y-axis and theta 509 deviate from the y-axis at +/−10 degrees. In FIG. 5C, phi 512 is on the x-axis and theta 510 and 511 deviate from the x-axis at +/−10 degrees. This type of non-planar rotation is analogous to adjusting the cranial-caudal angle of the C-arm system 1, in FIGS. 1A and/or 1B, during C-arm rotation about the examination subject in a 3-dimensional capable angiographic imaging system.

Two of the factors that are weighed when planning the range of the deflection in this type of a non-planar image data acquisition path are the area into which the metal artifacts is spread and the impact on the size of the volume for which full image construction is possible. FIGS. 6A, 6B and 6C illustrate the region wherein planar beam hardening, or streaking, effects created by the metal artifacts. The top view of the planar path 601 in FIG. 6A is similar to the top view of a non-planar image data acquisition path shown in FIGS. 7A and 8A, described below in detail. The planar streaking region 602 is the region affected by beam hardening artifacts, or metal artifacts, due to the presence of a dense, radio-opaque object located at iso-center. FIG. 6B illustrates the side view of the planar path 603 passing through the planar streaking region 604 created by beam hardening. As seen in FIGS. 6B and 6C, the planar streaking region is dense and degrades the quality of 3-dimensional images. FIG. 6C illustrates a top view of the planar path 605 passing through the planar streaking region 606.

Figure 8C:
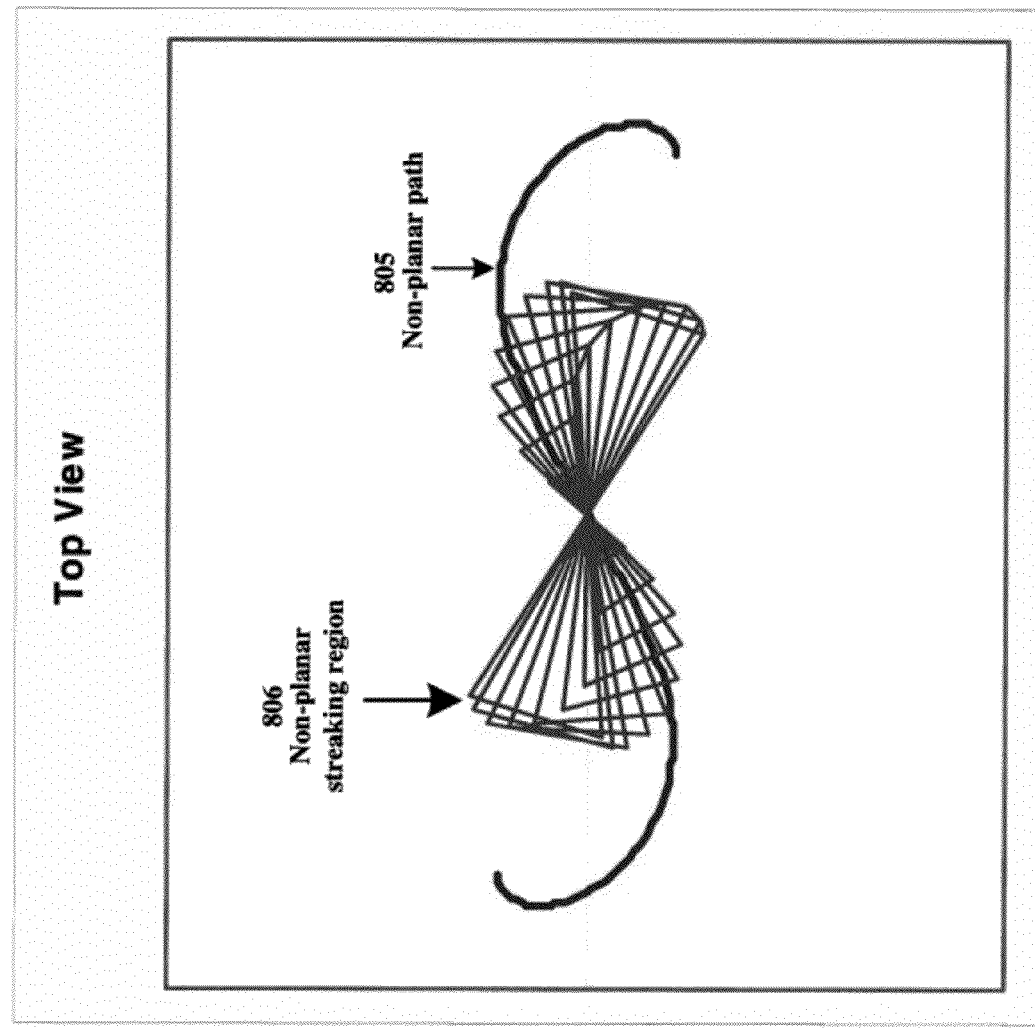
FIG. 8C illustrates a top view of an additional non-planar scan path and streaking created by effects of metal artifacts.
Figure 9D:
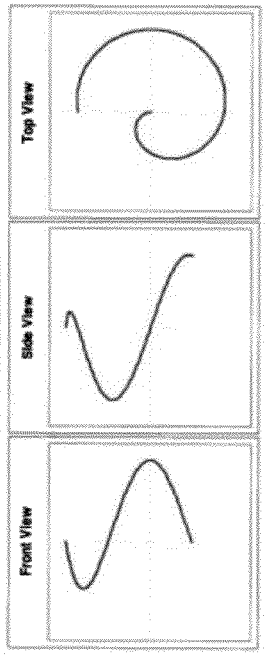
FIG. 9A-9F each illustrates a front, side and top view of non-planar scan paths.
Figure 9E:
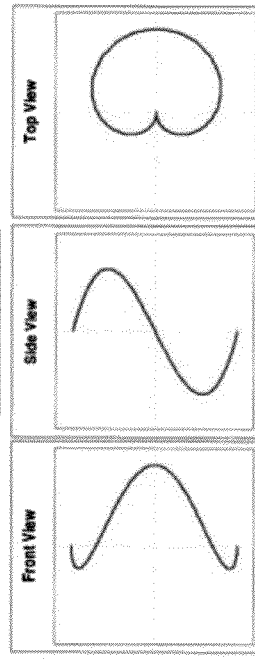
Figure 9F:
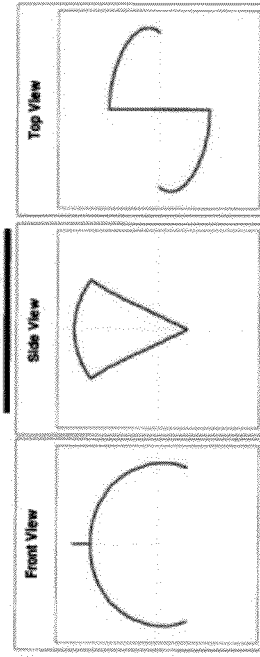
Figure 9A:
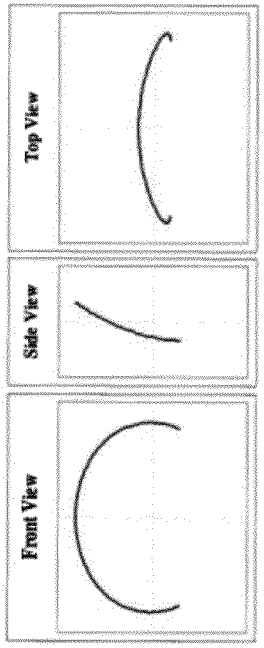
Figure 9B:
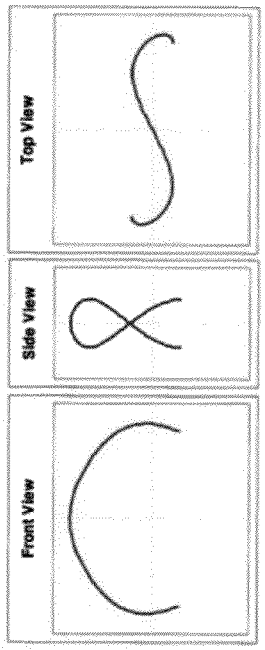
Figure 9C:
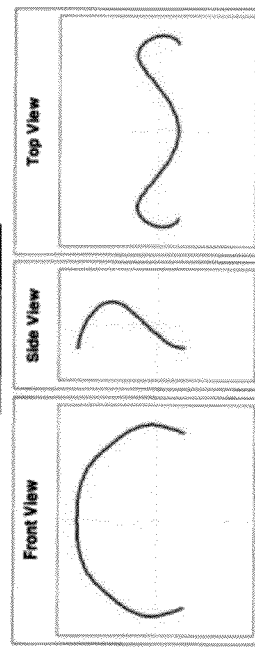

FIGS. 7A, 7B and 7C illustrate an example of a non-planar image data acquisition path. In these figures, a dense, radio-opaque object is located at iso-center. FIG. 7A illustrates a front view of the non-planar path 701. In this front view, the non-planar streaking region 702 created by the effects of metal artifacts is similar to the streaking region of a planar path. However, the side view shown in FIG. 7B of the non-planar path 703 illustrates the advantages of this system over the planar path systems. The non-planar streaking region 704 created by the effects of the metal artifacts is not concentrated in one plane, as in the planar acquisition path. Rather, the streaking is distributed throughout different planes and therefore, the overall effect of the beam hardening artifacts is reduced as compared to FIG. 6B. Therefore, as the non-planar streaking region 704 is not focused on a single plane and is instead extended onto multiple planes thereby reducing the overall effect of the beam hardening artifacts in a particular image projection used to construct a 3D image. This in turn greatly increases the quality of the 3-dimensional x-ray image created from the acquired the image data. Similarly, FIG. 7C illustrates a top view of the non-planar path 706 and the reduction of effects created by the metal artifacts shown as the non-planar streaking region 705. Although the overall content volume of the non-planar streaking is not decreased when compared to the volume of planar streaking, the streaking is spread throughout multiple planes which reduces the effect the streaking has on the 3D image constructed from the acquired image data. The non-planar image data acquisition path outperforms the planar acquisition path by distributing the metal artifacts over a greater volume, further diffusing the streaking artifacts. When image data is captured at a plurality of points along the non-planar path 706, the overall effects of the metal artifacts are minimized in comparison to FIG. 6C A further example of a non-planar image data acquisition path and the effects of metal artifact streaking are shown in FIGS. 8A, 8B and 8C. A dense radio-opaque object is located at iso-center in the views shown in these figures. FIG. 8A illustrates a front view of the non-planar path 801 and the non-planar streaking region 802. This view is similar to FIGS. 6A and 7A. FIG. 8B illustrates a side view of non-planar path 803. The non-planar streaking region 804 in this example is spread throughout multiple planes and is better distributed than the planar streaking region 604 in FIG. 6B. FIG. 8C illustrates the top view of the non-planar path 805 and the non-planar streaking region 806 created. As the streaking is distributed throughout multiple planes and is not concentrated in a single plane, as in FIGS. 6A-6C, the quality of the 3-dimensional x-ray image is improved over similar images constructed from image data acquired at points along a planar path. The acquisition of image data in a non-planar path provides multiple image projections in a plurality of different images planes each having a less data attributable to beam hardening and more data attributable to target tissue area.

FIGS. 9A-9F provides further exemplary non-planar image data acquisition paths. The front, side and top views of each of these figures are shown. These figures showing non-planar image data acquisition paths are advantageous over planar paths because streaking produced by metal artifacts is more evenly distributed which reduces the overall effect created by the metal artifacts. Different paths is chosen according to the various shapes and sizes of the radio-opaque objects within the examination subject and FIGS. 9A-9F are only shown as examples and do not limit the scope of the present system.

FIG. 10, flowchart 100 in step 101 shows that previously constructed 3-dimensional images are concurrently viewed by a user to determine if and where any radio-opaque objects are present. Alternatively, the previously constructed images may be displayed as 2-dimensional images, 3-dimensional images or a combination of 2-dimensional and 3-dimensional images. Images displayed in the third dimension described herein are used as an example only and are not meant to limit the spirit and scope of the invention. If it is determined that radio-opaque objects are present, a non-planar image data acquisition path for the x-ray imaging system is determined and used to minimize the effects created by the metal artifacts, as shown in step 102. In step 103, acquisition of the image data of the examination subject is initiated at a plurality of points along the non-planar image data acquisition path. In step 104, a 3-dimensional image is constructed from the acquired image data and in step 105, the 3-dimensional image is displayed, in accordance with the steps presented. If it is determined that radio-opaque objects are not present in the examination subject being examined in step 101, a non-planar or planar image data acquisition path is determined and set for the x-ray imaging system and acquisition of the image data of the examination subject is initiated, as shown in step 106. A 3-dimensional image is constructed, as shown in step 104 and displayed, as shown in step 105.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

A functional block diagram 1100 detailing the interactions of system components is shown in FIG. 11. User 1108 desires to acquire x-rays of examination subject 1101. Examination subject 1101, containing a radio-opaque object 1103 within, rests on an examination subject support 1102. In one embodiment, the user 1108 selectively orients the x-ray imaging system having a variable 3-dimensional acquisition axis and determines that a non-planar image data acquisition path for the x-ray imaging system is set. The user 1108 may issue the command to set the non-planar image data acquisition path through a graphical user interface (UI) 1107. The UI 1107 communicates with and issues control commands to the control computer 7. The control computer 7 may include control processor 1105 and an image processor 1106. The control processor 1105 sets the non-planar image data acquisition path for the x-ray imaging system and changes the 3-dimensional acquisition axis along the non-planar image data acquisition path. The x-ray imaging system 1104 sets the non-planar image data acquisition path for the C-arm and radiation detector (not shown) and acquires image data long the non-planar image data acquisition paths. The acquired image data may include image data acquired at multiple angles along the non-planar image data acquisition path. The acquired image data is sent to the control computer 7 and to the image processor 1106. The image processor 1106 constructs 3-dimensional image(s) from the acquired image data. Multiple images acquired at various angles and various planes along the non-planar image data acquisition path are collected and constructed from the acquired image data, thereby providing additional views with different metal artifact patterns. These multiple images are collected and constructed in order to provide the 3-dimensional image such that any introduced metal artifacts are minimized. Images are interpolated and constructed in a way to provide a 3-dimensional image with the minimized metal artifacts. Although implementing a non-planar image data acquisition path may not completely remove metal artifacts, the effects of the metal artifacts are minimized by diffusing the metal artifacts into other planes which more evenly distributes the streaking created by the effects of metal artifacts and allowing additional good projection data (free of metal artifacts) to be collected for areas adjacent to the radio-opaque object. Existing improvements employed to reduce overall beam hardening and scatter artifacts in 3-dimensional images can still be employed to further reduce the overall metal artifacts in 3-dimensional images constructed from non-planar image data acquisitions. The 3-dimensional image(s) are output to a monitor 1109 and are viewed by the user 1108.

In one embodiment of the present invention, a user may selectively set a non-planar image data acquisition path through the UI 1107 by selecting one or more of the following: (a) a list of preset acquisition paths; (b) an adjusted orientation of the 3-dimensional acquisition axis of the x-ray imaging system that is adjusted based on the location of the radio-opaque object the examination subject in relation to the x-ray imaging system; (c) a previously set 3-dimensional acquisition axis of a non-planar image data acquisition path extracted from previously acquired image data; and (d) a region of interest and have the x-ray imaging system automatically determine the non-planar image data acquisition path based on the region. The list of preset non-planar image data acquisition paths is stored in a data repository in the control computer 7. The list is presented to the user as a menu of user selectable image elements on the UI 1107. A user selectable image element is a visual representation of control data used in controlling the operation of the x-ray imaging system. Selection of a respective image element controls operation of the control computer 7 and initiates operation of an executable application for controlling operation of the x-ray imaging system. Upon selection of one of the preset non-planar image data acquisition paths via the UI 1107, a control signal including the control data is communicated to the control processor 1105 of the control computer 7. The control processor interprets the control data and signals the x-ray imaging system to operate and acquire images in accordance with the control data corresponding to the selected preset non-planar image data acquisition path. The x-ray imaging system automatically positions the C-arm 3 and/or the components of the C-arm system 1 in response to the control data generated in response to the selection of a non-planar image data acquisition path. The positioning of the x-ray imaging system includes, but is not limited to, movement of the multi-axis robot 2, movement of the C-arm 3, movement of the x-ray source 4 and movement of the radiation detector 5 in FIG. 1A. Additionally, as needed, once the x-ray imaging system is moved into the position that enables the x-ray system to move along the selected non-planar image acquisition path, the user further manually makes "fine tuning" adjustments.

In a healthcare environment, some factors are present that can interfere or cause collisions with the x-ray imaging system adjusted along the set non-planar image data acquisition path that can cause the x-ray imaging system to not properly acquire the required image data. Collisions with the examination subject, attending healthcare personnel and users, parts of the examination subject support, any impediments and other items that are present in the environment of the imaging system must be avoided. Prior to moving the x-ray imaging system along the non-planar image data acquisition path, the non-planar image data acquisition paths are evaluated to detect impediments that may interfere with the x-ray imaging system. Upon detection of an interfering impediment, the non-planar image data acquisition path is adjusted to avoid the impediment. The system simulates the non-planar image data acquisition paths to determine an optimal acquisition path. Known and proprietary collision-avoidance algorithms are used in combination with any of the above-described alternatives for positioning the x-ray imaging system along a non-planar image data acquisition path that preclude the C-arm 3 of the robotic C-arm system 1 for moving through, or assuming, a position at which a collision occur.

The system is applicable to angiography or CT imaging systems modified or designed to support non-planar acquisition paths. Existing flat detector angiographic imaging systems are capable of acquiring CT data sets of the examination subject, providing the benefits of CT imaging to diagnostic and interventional procedures. These systems acquire CT data by rotating the flat detector and x-ray source around the examination subject's anatomy. To date, this rotation has been confined, by angiographic imaging system design, to occur within a single plane perpendicular to the long axis of the examination subject. In accordance with the present invention, angiographic imaging systems are not so constrained and are able to support non-planar rotation paths about the examination subject.

While this invention is discussed in relation to a fluoroscopic imaging system, it should be noted that it is also applicable to CT imaging systems. Current CT imaging systems consist of a ring that rotates about the subject, where the source and detectors are fixed to the ring. In one embodiment, the positions of the source and detector perpendicular to the plane of the ring are adjusted, as the ring is rotated.

The systems and processes described are not exclusive. Other systems and processes are derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The processes and applications may, in alternative embodiments, be located on one or more (e.g., distributed) processing devices accessing a network linking the elements of FIG. 1 or 11. Further, any of the functions and steps provided in FIGS. 1-11 may be implemented in hardware, software or a combination of both and may reside on one or more processing devices located at any location of a network linking the elements of FIGS. 1 and 11 or another linked network, including the Internet.

What is claimed is:

1. A method for medical image processing and 3-dimensional image construction of an examination subject, comprising the activities of:

enabling a user to selectively orient an x-ray imaging system having a variable 3-dimensional acquisition axis relative to an examination subject support for holding an examination subject;

setting a non-planar image data acquisition path including a radio-opaque object within the examination subject for the x-ray imaging system oriented around the variable 3-dimensional acquisition axis in response to user instruction;

initiating acquisition of image data representing, a plurality of images of the examination subject including a radio-opaque object within the examination subject by the x-ray imaging system at a corresponding plurality of points along the non-planar image data acquisition path and a plurality of images of the examination subject excluding said radio-opaque object at a corresponding plurality of points along the non-planar image data acquisition path;

constructing a 3-dimensional image from the acquired image data both including and excluding said radio-opaque object such that image artifacts introduced by said radio-opaque object within the examination subject are diffused over a volume and reduced; and displaying the 3-dimensional image.

2. The method of claim 1, wherein the activity of constructing includes collecting and constructing multiple images acquired along various angles and planes along the non-planar image data acquisition path from the acquired image data in order to provide the 3-dimensional image such that any introduced artifacts are minimized.

3. The method of claim 1, wherein the activity of setting includes providing a user interface to a user to select the non-planar image data acquisition path by selecting at least one of:

a. a list of preset acquisition paths; and b. a region of interest and having the x-ray imaging system automatically determine the acquisition path based on said region.

4. The method of claim 1, wherein the activity of initiating acquisition includes one of:

a. enabling a user to move the examination subject support in a cranial-caudal direction allowing the x-ray imaging system to acquire image data at a plurality of points along the non-planar image data acquisition path; or b. automatically moving the x-ray imaging system in a cranial-caudal direction allowing the x-ray imaging system to acquire image data at a plurality of points along the non-planar image data acquisition path.

5. The method of claim 1, wherein the activity of initiating acquisition includes enabling a user to move the examination subject support and automatically moving the x-ray imaging system in coordination with each other in a cranial-caudal direction allowing the x-ray imaging system to acquire image data at a plurality of points along the non-planar image data acquisition path and including the steps of initiating acquisition of image data representing a plurality of images of the examination subject including said radio-opaque object at a corresponding plurality of points along a planar image data acquisition path and constructing said 3-dimensional image from the acquired image data comprising images acquired on the non-planar and planar image data acquisition paths.

6. The method of claim 1, wherein the activity of setting the non-planar image data acquisition path includes evaluating non-planar image data acquisition paths to detect impediments in the non-planar image data acquisition path and adjusting the non-planar image data acquisition path in response to any detected impediments to avoid the impediment.

7. The method of claim 6, wherein the activity of evaluating includes simulating non-planar image data acquisition paths to determine an optimal acquisition path.

8. The method of claim 1, wherein the activity of initiating acquisition includes enabling a user to coordinate rotational and orbital movement of the x-ray imaging system to acquire image data at a plurality of points along the non-planar image data acquisition path.

9. The method of claim 1, wherein the x-ray imaging system includes a C-arm having a radiation detector and an x-ray source facing each other on opposing ends of the C-arm and a multi-axis robot device connected to the C-arm providing the C-arm with 360 degree range of motion.

10. The method of claim 1, wherein the activity of setting further comprises the activities of:
  presenting a menu of a plurality of preset non-planar image data acquisition paths;
  enabling user selection of one of the preset non-planar image data acquisition paths for obtaining the 3-dimensional image; and
  automatically positioning the x-ray imaging system in response to the selected non-planar image data acquisition path.

11. The method of claim 1, wherein the activity of enabling a user includes enabling the user to concurrently view previously constructed images of the examination subject to determine whether any radio-opaque objects are present.

12. The method of claim 11, wherein the previously constructed images are at least one of:
  a. 3-dimensional images;
  b. 2-dimensional images; and
  c. a combination of 2-dimensional and 3-dimensional images.

13. A method for medical image processing and 3-dimensional image construction of an examination subject, comprising the activities of:
  enabling a user to selectively orient an x-ray imaging system having a variable 3-dimensional acquisition axis relative to an examination subject support for holding an examination subject;
  setting a non-planar image data acquisition path including a radio-opaque object within the examination subject for the x-ray imaging system oriented around the variable 3-dimensional acquisition axis in response to user instruction;
  initiating acquisition of image data representing a plurality of images of the examination subject including a radio-opaque object within the examination subject by the x-ray imaging system at a corresponding plurality of points along the non-planar image data acquisition path;
  constructing a 3-dimensional image from the acquired image data such that image artifacts introduced by said radio-opaque object within the examination subject are diffused over a volume and reduced; and
  displaying the 3-dimensional image
  wherein the activity of setting includes adjusting the 3-dimensional acquisition axis by automatically changing the non-planar image data acquisition path to minimize introduced metal artifacts and including the activity of selecting said non-planar image data acquisition path from a plurality of paths in response to size or shape of said radio-opaque object.

14. A system for medical image processing and 3-dimensional image construction of an examination subject comprising:
  a support surface on which an examination subject is placed;
  an x-ray imaging system for acquiring image data, the x-ray imaging system having a variable 3-dimensional acquisition axis relative to the examination subject on said support surface;
  a control processor electrically coupled to the x-ray imaging system for enabling a user to selectively set a non-planar image data acquisition path including a radio-opaque object within the examination subject for the x-ray imaging system oriented around the variable 3-dimensional acquisition axis and initiating acquisition of image data representing, a plurality of images of the examination subject including a radio-opaque object within the examination subject by the x-ray imaging system at a corresponding plurality of points along the non-planar image data acquisition path in response to user instruction and a plurality of images of the examination subject excluding said radio-opaque object at a corresponding plurality of points along the non-planar image data acquisition path;
  an image processor for constructing a 3-dimensional image from the acquired image data both including and excluding said radio-opaque object and image artifacts introduced by said radio-opaque object within the examination subject are diffused over a volume and reduced; and
  a monitor for displaying the 3-dimensional image.

15. The system of claim 14, wherein the image processor collects and constructs multiple images acquired along various angles and planes along the non-planar image data acquisition path from the acquired image data in order to provide the 3-dimensional image such that any introduced artifacts are minimized.

16. The system of claim 14, wherein the 3-dimensional acquisition axis is adjusted by automatically changing the acquisition path in order to minimize introduced metal artifacts and said control processor selects said non-planar image data acquisition path from a plurality of paths.

17. The system of claim 14, wherein the user selectively sets the non-planar image data acquisition path by selecting at least one of:
  a. a list of preset acquisition paths; and
  b. a region of interest and having the x-ray imaging system automatically determine the acquisition path based on said region.

18. The system of claim 14, wherein said examination subject support is moved by a user in a cranial-caudal direction allowing the x-ray imaging system to acquire image data at a plurality of points along the non-planar image data acquisition path.

19. The system of claim 14, wherein said control processor automatically causes said x-ray imaging system to move in a cranial-caudal direction allowing the x-ray imaging system to acquire image data at a plurality of points along the non-planar image data acquisition path.

20. The system of claim 14, wherein said examination subject support is moved by a user and said x-ray imaging system is automatically moved by said control processor in coordination with each other in a cranial-caudal direction allowing said x-ray imaging system to acquire image data at a plurality of points along the non-planar image data acquisition path.

21. The system of claim 14, wherein the control processor evaluates non-planar image data acquisition paths to detect impediments in the non-planar image data acquisition path and adjusting the non-planar image data acquisition path in response to any detected impediments to avoid the impediment.

22. The system of claim 21 wherein the evaluation of non-planar image data acquisition paths includes simulating non-planar image data acquisition paths to determine an optimal acquisition path.

23. The system of claim 14, wherein the x-ray imaging system includes a C-arm having a radiation detector and an x-ray source facing each other on opposing ends of the C-arm and a multi-axis robot device connected to the C-arm providing the C-arm with 360 degree range of motion.

24. The system of claim 14, wherein the x-ray imaging system includes a C-arm having a radiation detector and an x-ray source facing each other on opposing ends of the C-arm and a pedestal connected to the C-arm, said pedestal enabling orbital and rotational movement of said C-arm.

25. The system of claim 14, further comprising a user interface including an input mechanism for receiving a user instruction and wherein
    said control processor presents on said monitor a menu of a plurality of user-selectable preset non-planar image data acquisition paths and said x-ray imaging system is automatically positioned in response to the selected non-planar image data acquisition paths.

26. The system of claim 14, wherein said control processor provides previously constructed images of the examination subject viewed concurrently on said monitor to determine if and where any radio-opaque objects are present.

27. The system of claim 26, wherein the previously constructed images are at least one of:
    a. 3-dimensional images;
    b. 2-dimensional images; and
    c. combination of 2-dimensional and 3-dimensional images.

* * * * *